US009380970B2

(12) United States Patent
Christensen et al.

(10) Patent No.: US 9,380,970 B2
(45) Date of Patent: Jul. 5, 2016

(54) LANCET DEVICE WITH FLEXIBLE COVER

(71) Applicant: POPS! DIABETES CARE, INC., Stillwater, MN (US)

(72) Inventors: Curtis Jerome Christensen, Stillwater, MN (US); Daniel William Davis, Hugo, MN (US); Erik Daniel Davis, Hugo, MN (US)

(73) Assignee: POPS! Diabetes Care, Inc., Stillwater, MN (US)

(*) Notice: Subject to any disclaimer, the term of this patent is extended or adjusted under 35 U.S.C. 154(b) by 140 days.

(21) Appl. No.: 14/152,668

(22) Filed: Jan. 10, 2014

(65) Prior Publication Data

US 2014/0163341 A1 Jun. 12, 2014

Related U.S. Application Data

(63) Continuation of application No. 13/234,826, filed on Sep. 16, 2011, now Pat. No. 8,647,357.

(60) Provisional application No. 61/439,882, filed on Feb. 5, 2011.

(51) Int. Cl.
*A61B 5/1468* (2006.01)
*A61B 5/15* (2006.01)
*A61B 5/151* (2006.01)
(Continued)

(52) U.S. Cl.
CPC ............. *A61B 5/1468* (2013.01); *A61B 5/1411* (2013.01); *A61B 5/157* (2013.01); *A61B 5/150022* (2013.01); *A61B 5/15105* (2013.01); *A61B 5/15142* (2013.01); *A61B 5/15151* (2013.01); *A61B 5/15186* (2013.01); *A61B 5/150282* (2013.01); *A61B 5/150305* (2013.01); *A61B 5/150358* (2013.01); *A61B 5/150412* (2013.01); *A61B 5/150572* (2013.01); *A61B 5/742* (2013.01); *A61B 5/15157* (2013.01); *A61B 5/15176* (2013.01); *A61B 5/150969* (2013.01); *A61B 5/150977* (2013.01)

(58) Field of Classification Search
None
See application file for complete search history.

(56) References Cited

U.S. PATENT DOCUMENTS

| 4,648,408 A | 3/1987 | Hutcheson et al. |
| 5,014,718 A | 5/1991 | Mitchen |

(Continued)

FOREIGN PATENT DOCUMENTS

| WO | WO 9309710 A1 | 5/1993 |
| WO | WO 2005000118 A1 | 1/2005 |
| WO | WO 2012119128 A1 | 9/2012 |

OTHER PUBLICATIONS

Invitation to Pay Additional Fees and Where Applicable, Protest Fee, mailed on Jul. 10, 2014 in PCT Application PCT/US2014/035507 filed Apr. 25, 2014, 6 pages.

(Continued)

*Primary Examiner* — Erik B Crawford
*Assistant Examiner* — Gary E Hollinden
(74) *Attorney, Agent, or Firm* — Fredrikson & Byron, P.A.

(57) ABSTRACT

The biological test kit is a device for drawing and, optionally, testing biological samples. The biological test kit is an array of lancets set in wells in a rigid base. Each lancet well is covered by a protective cover which when deformed permits the lancet to puncture a user or other patient. In one embodiment the biological test kit employs distinct covers for each lancet and in another the covers are formed from sheet material formed into blisters which cover the lancet.

23 Claims, 7 Drawing Sheets

(51) Int. Cl.
  *A61B 5/157*   (2006.01)
  *A61B 5/00*    (2006.01)

(56) References Cited

U.S. PATENT DOCUMENTS

| | | | |
|---|---|---|---|
| 5,054,499 A | 10/1991 | Swierczek | |
| 5,070,886 A | 12/1991 | Mitchen et al. | |
| 5,139,029 A | 8/1992 | Fishman et al. | |
| 5,201,324 A | 4/1993 | Swierczek | |
| 5,231,993 A | 8/1993 | Haber | |
| 5,304,192 A | 4/1994 | Crouse | |
| 5,324,303 A | 6/1994 | Strong et al. | |
| 5,402,798 A | 4/1995 | Swierczek et al. | |
| 5,505,212 A | 4/1996 | Keljmann et al. | |
| 5,529,581 A | 6/1996 | Cusack | |
| 5,540,709 A | 7/1996 | Ramel | |
| 5,624,458 A | 4/1997 | Lipscher | |
| 5,630,828 A | 5/1997 | Mawhirt et al. | |
| 5,636,640 A | 6/1997 | Staehlin | |
| 5,709,699 A | 1/1998 | Warner | |
| 5,807,375 A | 9/1998 | Gross et al. | |
| 5,971,941 A | 10/1999 | Simons et al. | |
| 6,036,924 A | 3/2000 | Simons et al. | |
| 6,071,294 A | 6/2000 | Simons et al. | |
| 6,132,449 A | 10/2000 | Lum et al. | |
| 6,228,100 B1 * | 5/2001 | Schraga | 606/183 |
| 6,299,626 B1 | 10/2001 | Viranyi | |
| 6,302,855 B1 | 10/2001 | Lav et al. | |
| 6,364,890 B1 | 4/2002 | Lum et al. | |
| 6,472,220 B1 | 10/2002 | Simons et al. | |
| 6,553,244 B2 | 4/2003 | Lesho et al. | |
| 6,562,014 B2 | 5/2003 | Lin et al. | |
| 6,591,124 B2 | 7/2003 | Sherman et al. | |
| 6,679,852 B1 | 1/2004 | Schmelzeisen-Redeker et al. | |
| 6,706,159 B2 | 3/2004 | Moerman et al. | |
| 7,001,344 B2 | 2/2006 | Freeman et al. | |
| 7,150,755 B2 | 12/2006 | LeVaughn et al. | |
| 7,291,159 B2 | 11/2007 | Schmelzeisen-Redeker et al. | |
| 7,374,949 B2 | 5/2008 | Kuriger | |
| 7,378,007 B2 | 5/2008 | Moerman et al. | |
| 7,537,571 B2 | 5/2009 | Freeman et al. | |
| 7,544,185 B2 | 6/2009 | Bengtsson | |
| 7,666,149 B2 | 2/2010 | Simons et al. | |
| 7,771,367 B2 | 8/2010 | Haar et al. | |
| 7,846,110 B2 | 12/2010 | Kloepfer et al. | |
| 7,959,581 B2 | 6/2011 | Calasso et al. | |
| 8,142,465 B2 | 3/2012 | Jankowski et al. | |
| 8,172,867 B2 | 5/2012 | Nicholls | |
| 8,211,036 B2 | 7/2012 | Schraga | |
| 8,211,038 B2 | 7/2012 | Wang et al. | |
| 8,221,332 B2 | 7/2012 | Robbins et al. | |
| 8,333,712 B2 | 12/2012 | Imamura et al. | |
| 8,372,105 B2 | 2/2013 | Nishiuchi et al. | |
| 8,469,984 B2 | 6/2013 | Ruan et al. | |
| 8,469,985 B2 | 6/2013 | Nishiuchi | |
| 8,647,357 B2 | 2/2014 | Christensen et al. | |
| 8,808,202 B2 | 8/2014 | Brancazio | |
| 8,870,903 B2 | 10/2014 | LeVaughn et al. | |
| 8,926,644 B2 | 1/2015 | Schiff et al. | |
| 8,961,901 B2 * | 2/2015 | Glauser et al. | 422/503 |
| 9,101,302 B2 | 8/2015 | Mace et al. | |
| 2002/0087180 A1 | 7/2002 | Searle et al. | |
| 2003/0050573 A1 | 3/2003 | Kuhr et al. | |
| 2003/0088191 A1 | 5/2003 | Freeman et al. | |
| 2003/0153939 A1 * | 8/2003 | Fritz et al. | 606/181 |
| 2003/0191415 A1 | 10/2003 | Moerman et al. | |
| 2004/0236251 A1 * | 11/2004 | Roe | A61B 5/1411 600/583 |
| 2005/0085840 A1 | 4/2005 | Yi et al. | |
| 2005/0234491 A1 | 10/2005 | Allen et al. | |
| 2006/0058827 A1 | 3/2006 | Sakata | |
| 2006/0184189 A1 | 8/2006 | Olson et al. | |
| 2007/0112281 A1 | 5/2007 | Olson | |
| 2007/0129620 A1 | 6/2007 | Krulevitch et al. | |
| 2007/0293882 A1 | 12/2007 | Harttig et al. | |
| 2008/0058726 A1 | 3/2008 | Jina et al. | |
| 2009/0099427 A1 | 4/2009 | Jina et al. | |
| 2009/0204027 A1 * | 8/2009 | Zuk et al. | 600/583 |
| 2009/0259146 A1 | 10/2009 | Freeman et al. | |
| 2010/0023045 A1 * | 1/2010 | Macho et al. | 606/182 |
| 2010/0292609 A1 * | 11/2010 | Zimmer et al. | 600/583 |
| 2011/0040317 A1 | 2/2011 | Lee et al. | |
| 2011/0270129 A1 | 11/2011 | Hoerauf | |
| 2012/0302919 A1 | 11/2012 | Robbins et al. | |
| 2014/0011288 A1 * | 1/2014 | Kramer et al. | 436/164 |
| 2014/0170761 A1 | 6/2014 | Crawford et al. | |

OTHER PUBLICATIONS

International Search Report and Written Opinion mailed on Sep. 19, 2014, in PCT Application PCT/US2014/035507 filed Apr. 25, 2014, 17 pages.

Non-Final Office Action mailed on Jan. 5, 2015 in U.S. Appl. No. 13/946,838, filed Jul. 19, 2013, 17 pages.

International Preliminary Report on Patentability mailed on Apr. 1, 2015, in PCT Application PCT/US2014/035507 filed Apr. 25, 2014, 21 pages.

Non-Final Office Action mailed on Jul. 2, 2015 in U.S. Appl. No. 13/946,838, filed Jul. 19, 2013, 12 pages.

\* cited by examiner

LANCET DEVICE WITH FLEXIBLE COVER

CROSS REFERENCE TO RELATED APPLICATIONS

This application is a continuation of U.S. application Ser. No. 13/234,826, filed Sep. 16, 2011, which claims the benefit of U.S. Provisional Application No. 61/439,882, filed Feb. 5, 2011, the contents of each of which are hereby incorporated by reference in their respective entireties.

BACKGROUND

The biological test kit relates to the field of patient operated biological testing apparatus The use of Lancets in biological testing is well known in the art. In some inventions the Lancet is placed in or formed as part of a blister or bubble. A user causes the blister to collapse and thereby move the lancet to puncture the skin of the patient or user. U.S. Pat. No. 5,231,993 to Haber et al, U.S. Pat. No. 5,636,640 to Staehlin, U.S. Pat. No. 5,505,212 to Keljmann et al, U.S. Pat. No. 5,054,499 to Swierczeck, published patent applications 20080058726 to Jina, 20070129620 to Krulevich et al, and 20090099427 also to Jina are all typical of this approach. The present invention provides an array of lancets, each of which is housed and protected in a well which is covered by a flexible cover.

BRIEF SUMMARY OF THE INVENTION

The biological test kit is a device for drawing and, optionally, testing biological samples. The biological test kit comprises: a rigid first layer, one or more lancets secured to the rigid first layer, said lancets each having a sharp region disposed substantially away from the rigid first layer, one or more second layers disposed in an opposed arrangement relative to the rigid first layer, the rigid first layer and second layers being arranged to form one or more cavities, each of the one or more second layers forming one or more covers, each cover over one of the lancets; and each of the one or more covers having a first unconstrained configuration in which the lancet sharp region does not protrude past or through the cover and having a second compressed configuration in which the lancet's sharp region protrudes through the cover. In one embodiment the biological test kit employs distinct covers for each lancet and in another the covers are formed from sheet material formed into blisters which cover the lancet.

DETAILED DESCRIPTION OF THE INVENTION

Figure 1:
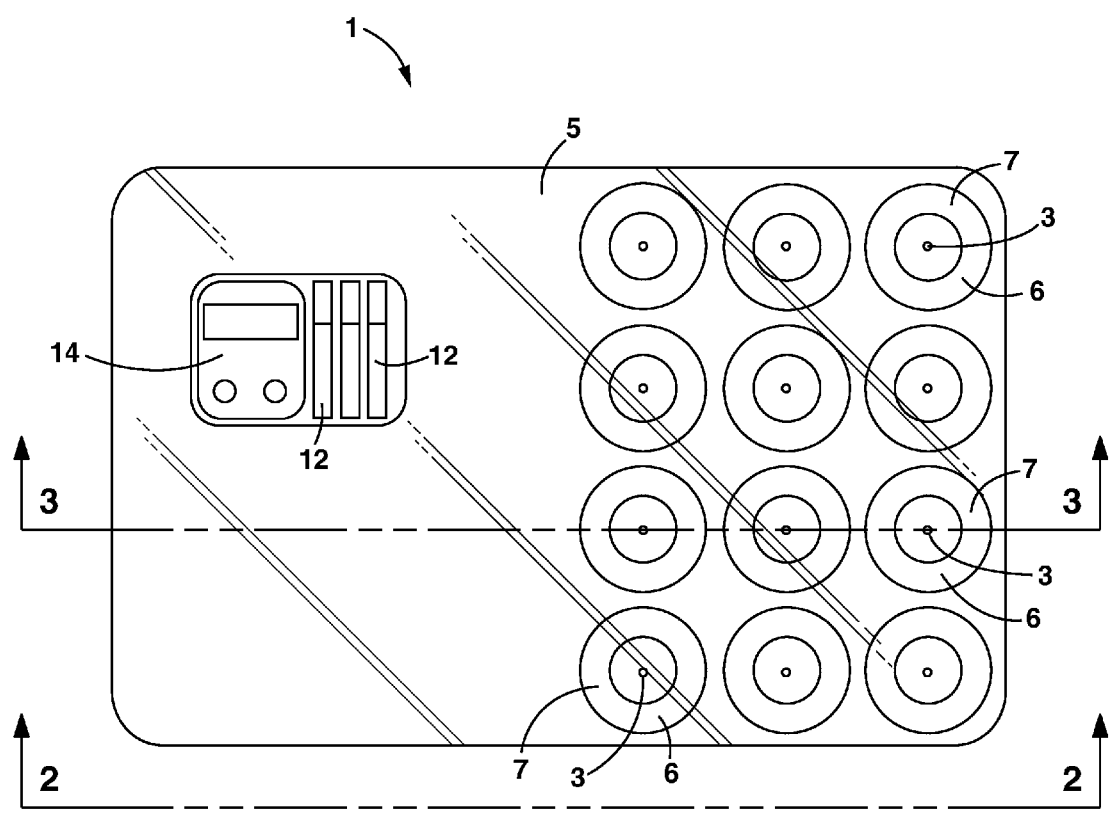
FIG. 1 is a top view of the biological test kit.
Figure 2:
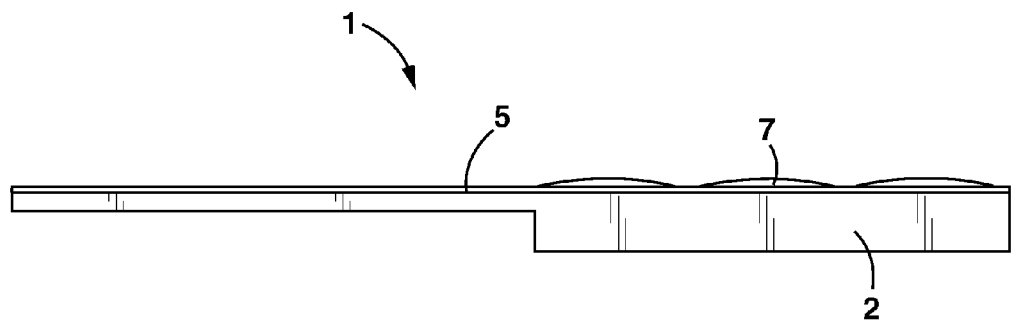
FIG. 2 is a front view taken from FIG. 1.
Figure 3:
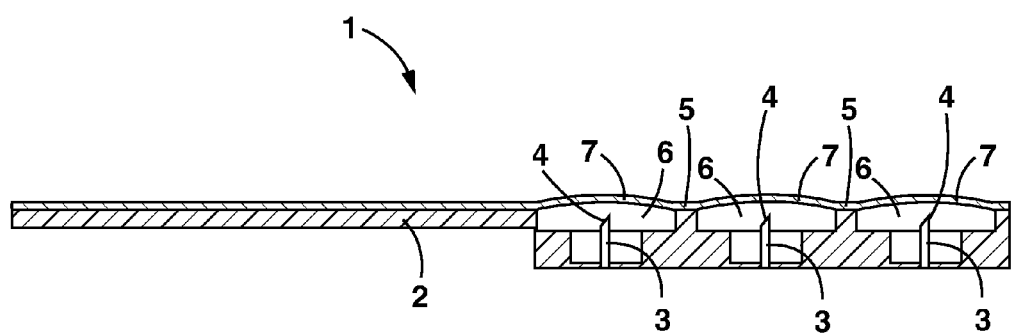
FIG. 3 is a section view taken from FIG. 1.
Figure 4:
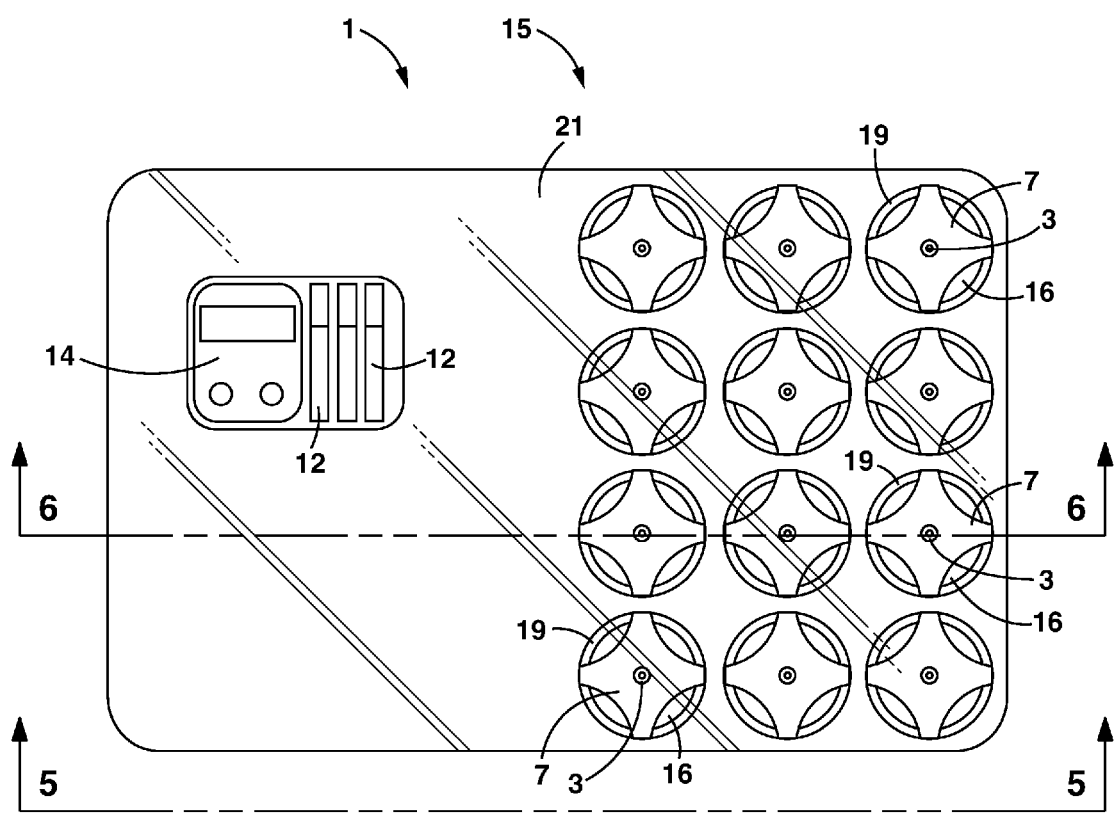
FIG. 4 is a second embodiment of a biological test kit.
Figure 5:
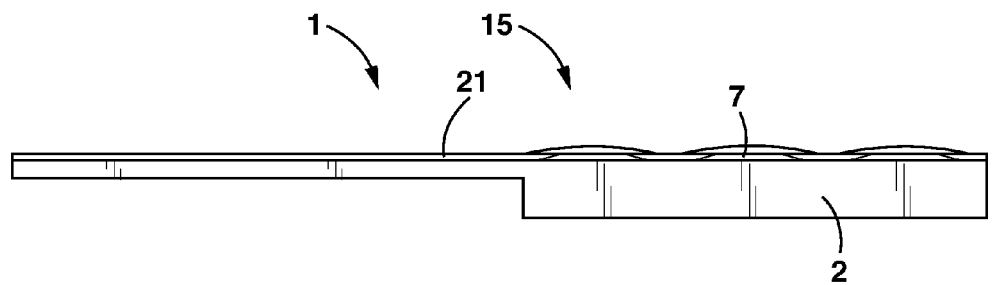
FIG. 5 is a front view taken from FIG. 4.
Figure 6:
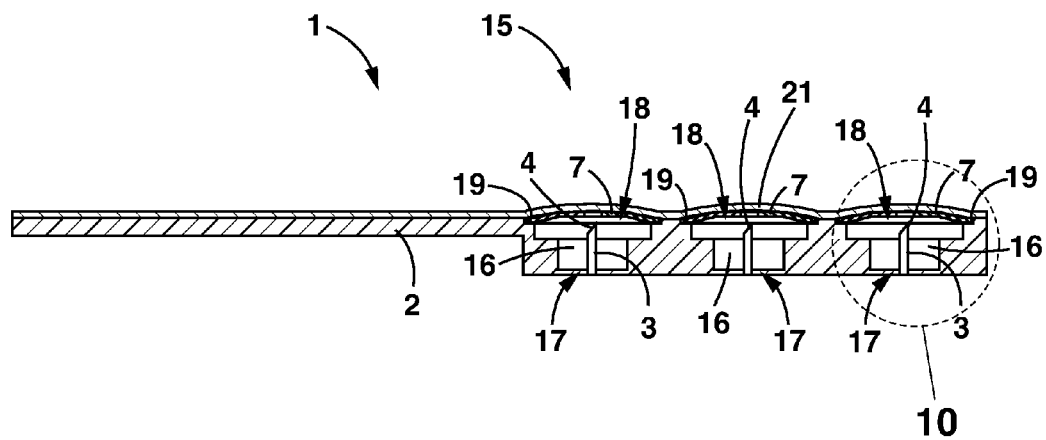
FIG. 6 is a section view taken from FIG. 4.
Figure 7:
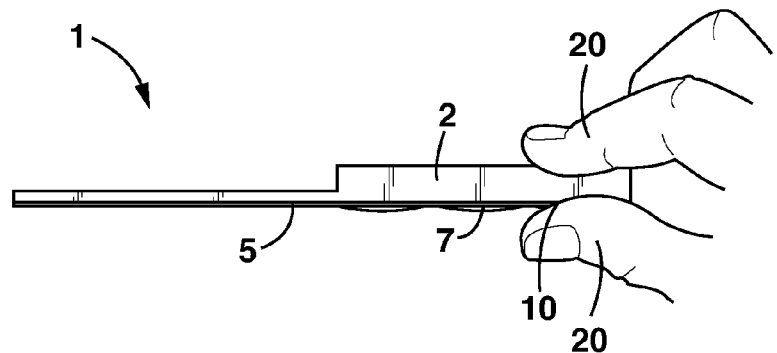
FIG. 7 is a front view of a kit pressed between a thumb and index finger.
Figure 8:
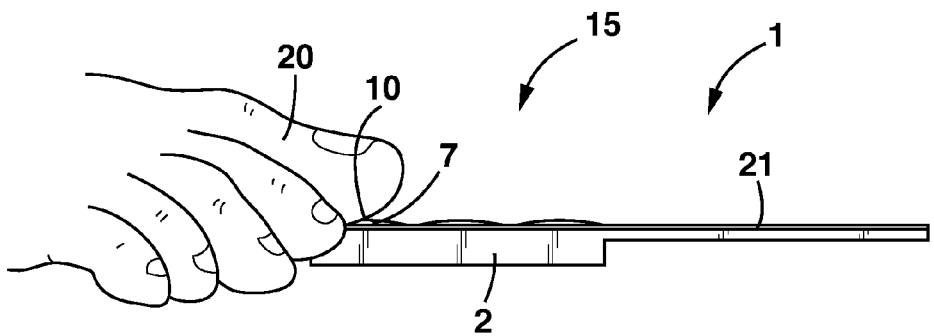
FIG. 8 is a front view of a second embodiment pressed upon a hard surface by another body part.
Figure 9:
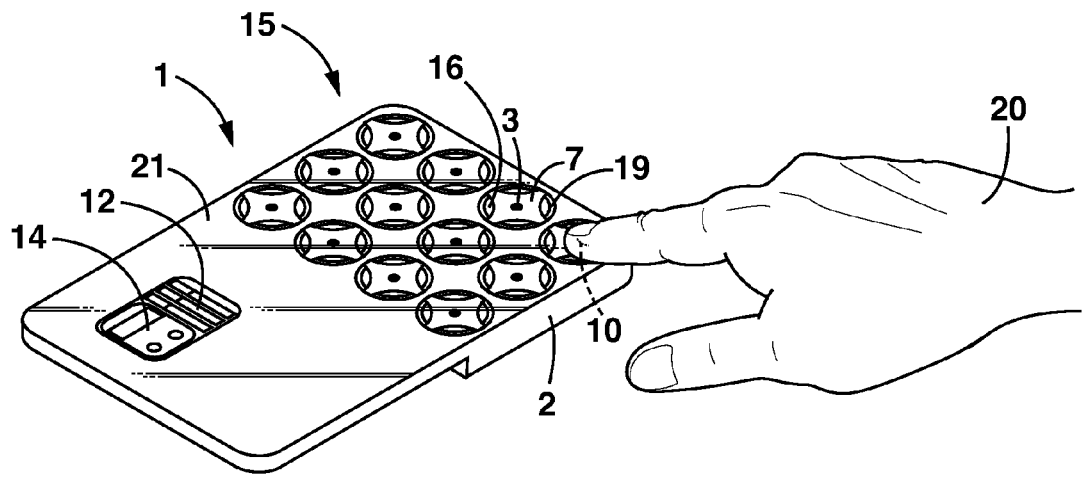
FIG. 9 is a perspective view of a second embodiment in use.
Figure 10:
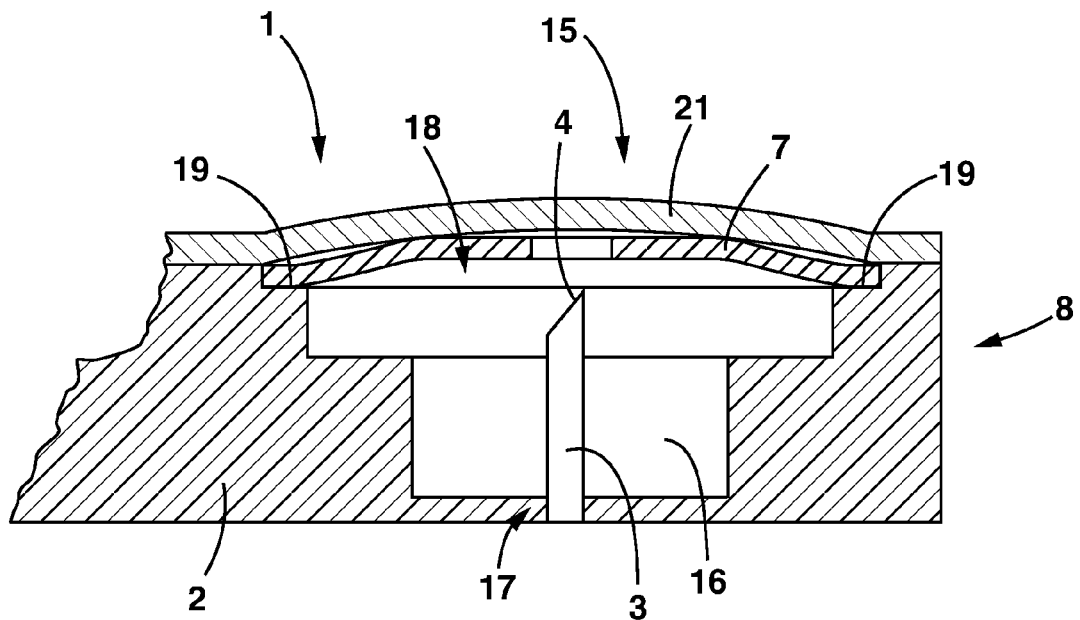
FIG. 10 is an enlarged detail view taken from FIG. 6, in unconstrained configuration.
Figure 11:
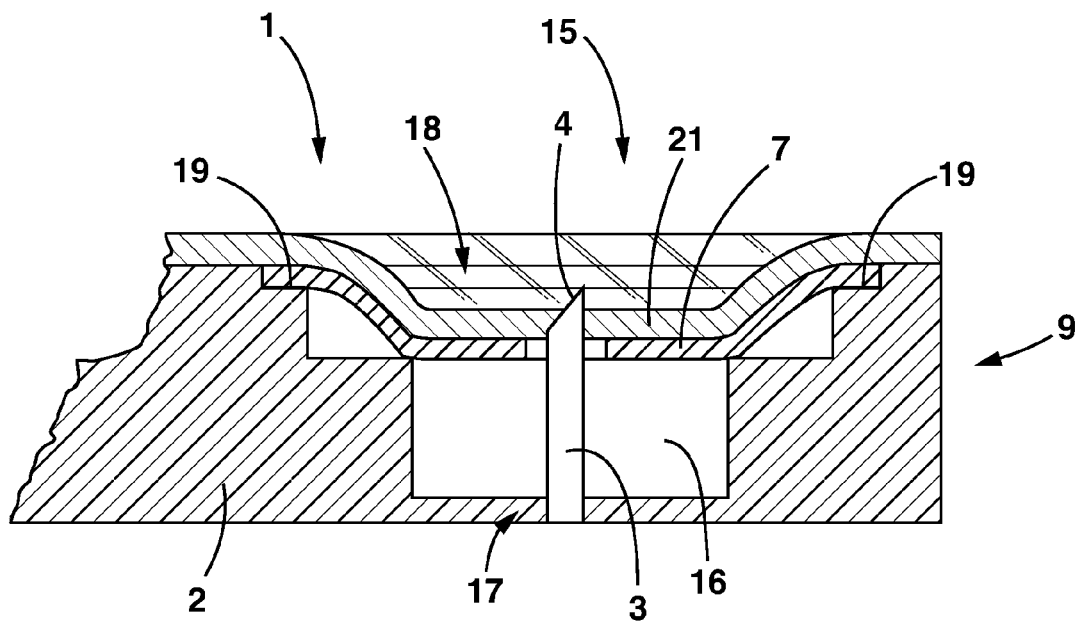
FIG. 11 is a view like FIG. 10 in a compressed configuration.
Figure 12:
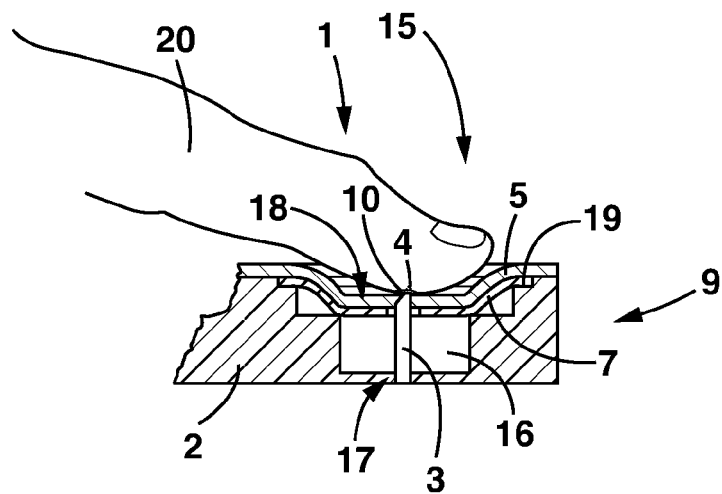
FIG. 12 is a detail view of collecting the biological sample by producing a wound.
Figure 13:
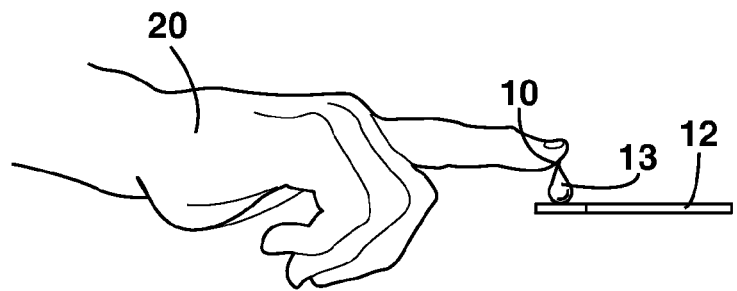
FIG. 13 is a front view of collecting a biological sample from a wound.
Figure 14:
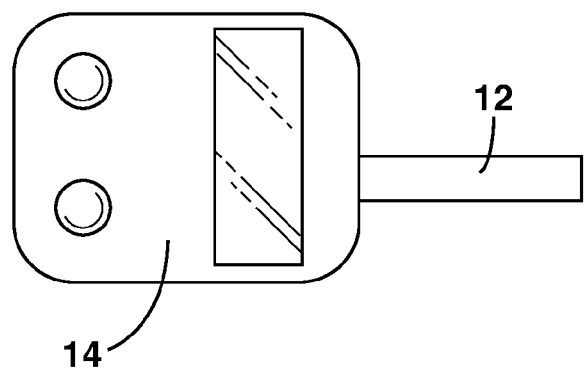
FIG. 14 is a top view of the testing apparatus measuring a sample.

The biological test kit 1 comprises: a rigid first layer 2, one or more lancets 3 secured to the rigid first layer 2, said lancets 3 each having a sharp region 4 disposed substantially away from the rigid first layer 2, one or more second layers 5 disposed in an opposed arrangement relative to the rigid first layer 2, the rigid first layer 2 and second layers 5 being arranged to form one or more cavities 6 there-between, each of the one or more second layers 5 forming one or more covers 7, each cover 7 over one of the lancets 3; and each of the one or more covers 7 having a first unconstrained configuration 8 in which the lancet 3 sharp region 4 does not protrude past or through the cover 7 and having a second compressed configuration 9 in which the lancet's 3 sharp region 4 protrudes through the cover 7.

The rigid first layer 2 is composed of a rigid material such as plastic, wood, or metal. The rigid first layer 2 provides a foundation for construction of the biological test kit 1.

Lancets 3 are small rods or bars constructed of metal or plastic with one end flattened and sharpened to facilitate making a small puncture site 10, often optimized for puncturing human skin. In the biological test kit 1, one or more lancets 3 are fixed in the rigid first layer 2 such that the sharp region 4 of the lancet 3 is positioned at a distance from the rigid first layer 2. The lancets 3 may be placed in any pattern.

The second layer 5 is made of resilient material and is formed over the rigid first layer 2 to provide a cover 7 for each of the lancets 3. This may be accomplished in any number of ways including, but not limited to, forming the second layer 5 into a number of blisters where each blister forms a cover 7 for one of the lancets 3 and forms an airtight cavity 6 covering and surrounding the lancet 3. These blisters are sized so that when a user applies sufficient compressive force against the rigid first layer 2 and the second layer 5 the blister is pierced by the lancet 3 along with the skin of the user. The user may accomplish this by pinching the blister between a thumb and index finger, or any other suitable body parts 20. Alternatively, the user may apply this pinching force by placing the rigid first layer 2 on a supporting surface and pressing the appropriate body part 20 on the blister. The material chosen for the second layer 5, and therefore the blisters, may be sufficiently resilient to cause the blister to reform into its original position, and cover 7 the lancet 3, when the user applied pressure is removed.

The biological test kit 1 may include any number of second layers 5. However, each of the second layers 5 may serve a unique purpose such as resealing the hole made by passage of the Lancet 3 through the cover 7 or providing a dose of antibiotic, or providing an indication as to the chemical analysis of the biological sample 13.

The biological test kit 1 may also include test strips 12 which capture biological samples 13 resulting from the action of the lancet 3 such as fluid exuded from the puncture site 10 created by the lancet 3.

The biological test kit 1 may also include a test apparatus 14 for analysis of the samples 13 gathered as above. This test apparatus 14 may include the ability to display the results of the analysis in any suitable manner, such as a digital readout or color change of the test strip 12.

In a second embodiment 15 the biological test kit 1 includes a rigid first layer 2 and lancets 3 as above with a distinct well 16 provided for each lancet 3 within the rigid first layer 2 and a distinct cover 7 for each lancet 3. Each well 16 has a closed end 17 and an open end 18. A lancet 3 is fixed to the closed end 17 of each well 16. Each well 16 is formed with a ledge 19 around the interior of its open end 18. The well 16 and the ledge 19 are sized to permit insertion of a cover 7 said cover 7 supported by the ledge 19.

Each cover 7 is formed as a compound curve and formed from a flexible and resilient material such that the cover 7 can be compressed by an applied force into a compressed configuration 9 and when said force is removed the cover 7 returns to its unconstrained configuration 8. When the cover 7 is placed in the well 16 with the convex surface facing away from the closed end 17 of the well 16 and the cover 7 is in the unconstrained configuration 8 the cover 7 conceals the lancet 3. When so placed and pressed into the compressed configuration 9 the lancet 3 protrudes through the cover 7 to a prescribed distance. When a user desires to produce a puncture site 10 from which a biological sample 13 may be taken, the user presses the cover 7 with sufficient force that the lancet 3 pierces the cover 7 and the user's finger, or other body part 20. It is to be noted that the cover 7 may or may not include a hole through which the lancet 3 passes.

The biological test kit 1 may be further provided with one or more protective or indicative layers 21. The protective or indicative layers 21 may be made of a material which is flexible yet non porous to prevent intrusion of foreign material when serving a protective function and made of a chemically reactive material when serving an indicative function or be made of a material suitable for protection and treated with an indicative substance to serve both purposes.

As above the rigid first layer 2 may be provided with a test apparatus 14 and test strips 12.

The biological test kit 1 may be used according to the following steps: collecting biological samples 13 comprising the steps, compressing a lancet 3 cover 7 onto a stationary lancet 3 until said lancet 3 pierces said cover 7 and said user, producing a puncture site 10. This method may further include the step of collecting biological samples 13 from said puncture site 10. This method may also comprise the step of using a testing apparatus 14 to measure one or more chemical properties of said biological sample 13.

What is claimed is:

1. A method of producing a wound in a body part of a user comprising the steps of:
    (a) the user positioning a device that includes (i) a rigid base, (ii) a stationary lancet secured to the rigid base and having a sharp region disposed substantially away from the rigid base, and (iii) a compressible lancet cover forming a cavity with the rigid base that covers the stationary lancet, the compressible lancet cover having a hole through which the stationary lancet is configured to pass; and
    (b) the user compressing the compressible lancet cover with a body part onto the stationary lancet, the stationary lancet remaining stationary relative to the rigid base, until said stationary lancet protrudes through said hole in said compressible lancet cover and pierces said body part without first piercing the compressible lancet cover or anything else, producing a wound in said body part.

2. The method of claim 1 further comprising the step of: (c) collecting a biological sample from said wounded body part.

3. The method of claim 1 further comprising the step of: (c) using a testing apparatus to measure one or more chemical properties of said biological sample.

4. The method of claim 1, further comprising the steps of:
    (c) the user bringing the wounded body part out of contact with the stationary lancet and the compressible lancet cover; and
    (d) the user applying a biological sample from the wounded body part to a separate and distinct test apparatus.

5. The method of claim 4, wherein the test apparatus is housed by the rigid base.

6. A device, comprising:
    (a) a rigid base;
    (b) a first stationary lancet secured to the rigid base and having a sharp region disposed substantially away from the rigid base; and
    (c) a first compressible lancet cover with a lancet hole, the first compressible lancet cover forming a first cavity with the rigid base that covers the first stationary lancet and being compressible from an unconstrained configuration in which the first stationary lancet's sharp region does not protrude through the lancet hole to a compressed configuration in which the first stationary lancet's sharp region protrudes through the lancet hole to the exterior of the first cavity without piercing the first compressible lancet cover or anything else inside the first cavity, wherein the first stationary lancet is stationary relative to the rigid base as the first compressible lancet cover is compressed to the compressed configuration.

7. The device of claim 6, wherein the rigid base includes a lancet region to which the first stationary lancet is secured and a separate test apparatus region that houses a test apparatus.

8. The device of claim 6, wherein the first compressible lancet cover has a convex surface that faces away from the rigid base when the first compressible lancet cover is in the unconstrained configuration.

9. The device of claim 8, wherein, when the first compressible lancet cover is compressed to the compressed configuration, the first stationary lancet protrudes through the lancet hole in the first compressible lancet cover to a prescribed distance.

10. The device of claim 8, wherein the rigid base includes a first well with a first ledge, and the first compressible lancet cover includes a support edge by which the first compressible lancet cover is supported by the first ledge to form the first cavity with the rigid base.

11. The device of claim 10, wherein the support edge of the first compressible lancet cover comprises a plurality of evenly spaced contact points that contact the first ledge.

12. The device of claim 10, wherein the first cavity includes at least one opening in the cavity near where the first compressible lancet cover meets the rigid base.

13. The device of claim 10, wherein the first stationary lancet extends from a closed end of the well, with the first stationary lancet's sharp region being disposed substantially away from the closed end of the well, wherein the first stationary lancet's sharp region is not farther away from the closed end of the well than is the first ledge.

14. The device of claim 6, wherein the device is without antibiotic or other liquids.

15. The device of claim 6, further comprising:
    (d) a second stationary lancet secured to the rigid base and having a sharp region disposed substantially away from the rigid base; and
    (e) a second compressible lancet cover with a lancet hole, the second compressible lancet cover forming a second cavity with the rigid base that covers the second stationary lancet and being compressible from an unconstrained configuration in which the second stationary lancet's sharp region does not protrude through the lancet hole to a compressed configuration in which the second stationary lancet's sharp region protrudes through the lancet hole to the exterior of the second cavity without piercing the second compressible lancet cover or anything else inside the second cavity, wherein the second stationary lancet is stationary relative to the rigid base as the second compressible lancet cover is compressed to the compressed configuration.

16. A method of lancing a body part of a user, comprising:
(a) placing a device on a supporting surface, the device including:
  (i) a rigid base,
  (ii) a stationary lancet secured to the rigid base and having a sharp region disposed substantially away from the rigid base, and
  (iii) a compressible lancet cover with a lancet hole, the compressible lancet cover forming a cavity with the rigid base that covers the stationary lancet; and
(b) pressing the compressible lancet cover with the body part to compress the compressible lancet cover from an unconstrained configuration in which the stationary lancet's sharp region does not protrude through the lancet hole to a compressed configuration in which the stationary lancet's sharp region protrudes through the lancet hole, thereby piercing the body part without piercing the compressible lancet cover or anything else inside the cavity, wherein the stationary lancet is stationary relative to the rigid base as the compressible lancet cover is pressed to the compressed configuration.

17. The method of claim 16, further comprising:
(c) bringing the body part out of contact with the stationary lancet and the compressible lancet cover; and
(d) applying a biological sample from the body part to a separate and distinct test apparatus.

18. The method of claim 17, wherein the device's rigid base includes a lancet region to which the stationary lancet is secured and a separate test apparatus region that houses the test apparatus.

19. The method of claim 18, wherein the device's compressible lancet cover has a convex surface that faces away from the rigid base when the compressible lancet cover is in the unconstrained configuration, and wherein, when the compressible lancet cover is compressed to the compressed configuration, the stationary lancet protrudes through the lancet hole in the compressible lancet cover to a prescribed distance.

20. The method of claim 16, wherein the body part is not brought into contact with antibiotic or other liquids.

21. The method of claim 16, wherein (i) the device's rigid base includes a well with a ledge, (ii) the compressible lancet cover includes a support edge by which the compressible lancet cover is supported by the ledge to form the cavity with the rigid base, and (iii) the stationary lancet's sharp region does not extend past the ledge.

22. The method of claim 21, wherein the support edge of the compressible lancet cover comprises a plurality of evenly spaced contact points that contact the ledge.

23. The method of claim 21, wherein the cavity includes at least one opening in the cavity near where the compressible lancet cover meets the rigid base.

* * * * *